United States Patent [19]

Jeandet et al.

[11] Patent Number: 6,080,701
[45] Date of Patent: Jun. 27, 2000

[54] USE OF ALUMINIUM CHLORIDE AS A RESVERATROL SYNTHESIS ELICITOR

[75] Inventors: Philippe Jeandet, Fontaine les Dijon; Roger Bessis; Marielle Adrian, both of Dijon; Jean-Claude Yvin; Jean-Marie Joubert, both of Saint Malo, all of France

[73] Assignee: Laboratoires Goemar S.A., Saint Malo Cedex, France

[21] Appl. No.: 09/068,343

[22] PCT Filed: Nov. 18, 1996

[86] PCT No.: PCT/FR96/01813

§ 371 Date: May 12, 1998

§ 102(e) Date: May 12, 1998

[87] PCT Pub. No.: WO97/18715

PCT Pub. Date: May 29, 1997

[30] Foreign Application Priority Data

Nov. 17, 1995 [FR] France .................................. 95 13642

[51] Int. Cl.$^7$ ...................................................... A01N 59/06
[52] U.S. Cl. ............................................................... 504/187
[58] Field of Search .............................................. 504/187

[56] References Cited

U.S. PATENT DOCUMENTS 5,043,005  8/1991  Keller et al. .................................. 71/65

*Primary Examiner*—S. Mark Clardy
*Attorney, Agent, or Firm*—Dennison, Scheiner, Schultz & Wakeman

[57] ABSTRACT

The use of aluminium chloride as a resveratrol synthesis elicitor in crop plants and edible products thereof, particularly in the field of vine and grape growing as well as in the production of grape juice and wine, is disclosed.

13 Claims, No Drawings

USE OF ALUMINIUM CHLORIDE AS A RESVERATROL SYNTHESIS ELICITOR

This application has been filed under 35 USC 371 as the national stage of international application PCT/FR96/01813 filed Nov. 18, 1996.

BACKGROUND OF THE INVENTION

The object of the present invention is the use of aluminium chloride as a resveratrol synthesis elicitor in crop plants and edible products thereof, and in particular vine, grapes, grape juice and wine.

It is known that certain plants, such as the vine in particular, can synthesise, in response to a stress such as an ultra-violet light ray irradiation or a parasitic infection, natural molecules which enable them to adapt themselves to this stress. One of the principal constituents of these natural molecules is resveratrol (trans-3,5,4'-trihydroxystilbene).

It is also known that resveratrol possesses particularly interesting pharmacological properties which are usable notably in the prevention or in the treatment of certain human illnesses.

Thus, this molecule which may also be extracted from the roots of *Polygonum cuspidatum* is used notably in popular traditional Chinese and Japanese medicine in the treatment of hyperlipemia, arteriosclerosis, inflammatory illnesses and allergic illnesses.

Various studies have in fact demonstrated that resveratrol decreases platelet aggregation and exerts a protective effect vis-à-vis the oxidation of plasma lipoproteins, these two latter factors being implicated in the mechanisms of artherothrombogenesis which can lead to myocardial infarction.

The protective effect of resveratrol vis-à-vis the oxidation of plasma lipoproteins is particularly high, since it has been demonstrated that this effect is much more significant than that procured by vitamin E ($\alpha$-tocopherol) which is considered to be a powerful natural anti-oxidising agent.

It has also been suggested that resveratrol could furnish a protection vis-à-vis cancer due to its anti-radical properties against free radicals implicated in the phenomena of cellular cancerisation.

Given the beneficial role exertable by resveratrol in the field of human health, it seems interesting to be able to have a simple means at one's disposal which enables increasing the resveratrol content of certain edible products.

SUMMARY OF THE INVENTION

It has been discovered in an entirely unexpected and surprising manner that aluminium chloride is capable of inducing the synthesis of resveratrol in crop plants with which it is placed in contact, as well as in their transformed products.

DETAILED DESCRIPTION OF THE INVENTION

The present invention is more particularly applied to the vine and its products which are grapes, grape juice and wine.

The invention can of course be applied also to any crop plant which naturally produces resveratrol, amongst which peanut may notably be cited.

This plant can be a shrub, as in a case of a vine, or even a tree.

The expression "product" used within the context of the present invention designates any product which originates naturally from the plant, notably such as the fruit, as well as any product resulting from further transformation treatments of the fruit.

According to a particular characteristic of the use in accordance with the invention, the aluminium chloride is applied via the foliar route and/or in the case of trees or shrubs, by injection into the trunks.

Advantageously, the aluminium chloride is applied in an amount of 0.1 to 100 kilograms, and preferably from 10 to 50 kilograms, per hectare of cultivated ground and per treatment.

Of course, the active doses which can be used will vary notably according to the plant, the climatic conditions, and to the application route selected.

In the case of the vine, the aluminium chloride will be applied preferably via the foliar route and in an amount of 0.5 to 50 kilograms, and preferably from 5 to 25 kilograms per hectare and per treatment.

The aluminium chloride can be applied at any stage of the culture of the plants concerned.

In the particular case of the vine, it will preferably be applied from flowering to the maturity of the grape berry.

Advantageously, and notably in every case in which it is desired to use aluminium chloride in the form of an aqueous solution, the aluminium chloride will be presented in hydrated form, and notably hexahydrated form.

According to another particular characteristic, the use according to the invention comprises the preparation of a composition which contains an effective amount of aluminium chloride optionally incorporated with a carrier or vehicle which is acceptable in agriculture.

Generally, this composition can be presented in a solid form, notably as powders, in particular wettable powders, or granules, or even, and preferably, in a liquid form, notably in the form of an aqueous solution.

In a particular embodiment, this composition can further contain at least one additional substance selected from the fungicides, insecticides, herbicides, growth hormones, deficiency correcting elements, as well as algae, or extracts of algae.

The extracts of algae which can be used within the context of the invention are for example a cream of algae, such as obtained by the implementation of the French patent number 74 35162.

Advantageously, a composition used in the context of the present invention will be presented in a solid form and will contain from 0.2 to 55% by weight of aluminium chloride.

Generally, the compositions which can be used within the context of the invention will be prepared by mixing aluminium chloride, in the form of a powder, with usual additives, for example solid fillers and/or solvents.

Surfactant substances, dispersing agents or emulsifying agents will also be used if it is necessary.

Kaolin or finely divided clay can be used for example as solid filler for the preparation of wettable powders or granules.

These compositions, when they are presented in liquid form, will preferably be obtained by dilution of hydrated aluminium chloride in water.

The preparation of pulverisable, oil-based or emulsifiable concentrate-based compositions can also be envisaged, notably in the case of mixtures with additional substances which are not soluble in water.

The present invention will be better understood upon reading the Examples that follow, which are given solely in a non-limiting way.

In these Examples, percentages are given by weight, unless otherwise indicated.

EXAMPLE 1

Demonstration of the Properties of Aluminium Chloride

In order to demonstrate the properties of aluminium chloride vis-à-vis the synthesis of resveratrol, various experiments were carried out on the vine.

More specifically, the extremities of seven month-old branches, originating from cuttings cultivated in greenhouses, and comprising seven internodes up to the apex, were plunged into aqueous solutions, at different aluminium chloride concentrations, for predetermined times and in the dark.

The presence of resveratrol may be observed under ultra-violet light at 366 nm, the resveratrol emitting a pale blue fluorescence under these conditions.

The amount of resveratrol produced in the leaves was then determined.

To this end, the leaves were taken and ground in 80% methanol.

The ground leaves thus obtained were filtered on a sintered glass n° 4.

The filtrate is then recovered and passed through a column of the seppack type of 1 cm in length.

The filtered thus obtained is evaporated under vacuum at +40° C. and the residue obtained is diluted in 20 milliliters of 95% methanol per gram of fresh weight of the sample.

The solution is then placed in a freezer at −20° C.

Every manipulation was carried out in the dark.

The amount of resveratrol extracted is quantified by chromatography.

The chromatography system is composed of a quaternary gradient controller, an automatic injector, a spectrofluorimeter and a visible UV detector with diode module.

A chromatography is carried out on a C18 column (25 cm×4.6 mm particle size: 4 μm).

The stationary phase (grafted silica) thus retains the organic molecules.

For these analyses, a solution of acetonitrile (40%) and ultra-pure water (60%) with a flow rate of 0.6 ml/min was used.

The resveratrol is detected simultaneously by UV spectrophotometry at 307 nm and by fluorimetry (excitation 340 nm and emission at 374 nm).

In order to standardise the chromatograph, a calibration curve is made by injecting various solutions of synthetic resveratrol at different concentrations (10 ng-20 ng-50 ng-100 ng-200 ng).

The straight line obtained possesses an excellent correlation coefficient $R_2=0.9950$.

The results obtained, expressed in micrograms of resveratrol per gram of extract, are given in Tables 1 to 5 below.

In each Table, the results of the tests are given which were carried out on two species of vine, namely *Vitis rupestris* and *Vitis vinifera*.

The results given in Table 1 were obtained after nine hours of soaking in the aluminium chloride solution, whilst the results given in Table 2, 3, 4 and 5 were obtained for soaking times of 15 hours 15, 17 hours 30, 22 hours and 26 hours, respectively.

These results clearly illustrate the elicitory power of aluminium chloride vis-à-vis the synthesis of resveratrol in the vine, the effect observed being particularly intense in relation to the Vitis rupestris species.

These results also enable predicting the elicitory effect of aluminium chloride vis-à-vis the synthesis of resveratrol in the grape and in wine, since a correlation exists between the production of resveratrol in the leaves and in the bunches of grapes.

In particular, it has been demonstrated that grapes (and in particular the grape skin) produce resveratrol, and that a direct relationship exists between the production of resveratrol in the leaves and in the bunches throughout the whole of the vegetative cycle of the vine.

TABLE I

| AlCl$_3$ concentration in % | AMOUNT OF RESVERATROL EXPRESSED IN μg/g OF FRESH EXTRACT OF: | |
|---|---|---|
| | V. rupestris | V. vinifera |
| Control | 0.454 | 0.80 |
| 0.6 | 61.51 | 1.60 |
| 0.8 | 118.474 | 113.70 |
| 1 | 217.604 | 1.94 |
| 1.5 | | 52.80 |
| 2 | 57.64 | 88.46 |
| 3 | 122.52 | 69.70 |
| 4 | 88.86 | 101.30 |

TABLE II

| AlCl$_3$ concentration in % | AMOUNT OF RESVERATROL EXPRESSED IN μg/g OF FRESH EXTRACT OF: | |
|---|---|---|
| | V. rupestris | V. vinifera |
| Control | 0.06 | 0.06 |
| 0.3 | 177.34 | 0.06 |
| 0.4 | 173.72 | 6.46 |
| 0.6 | 350.26 | 70.9 |
| 0.8 | 279.84 | 119.47 |
| 1 | 143.39 | 175.17 |
| 1.5 | 222.03 | 94.01 |
| 2 | 246.54 | 111.96 |
| 3 | 112.67 | 136.12 |
| 4 | | 95.48 |

TABLE III

| AlCl$_3$ concentration in % | AMOUNT OF RESVERATROL EXPRESSED IN µg/g OF FRESH EXTRACT OF: | |
|---|---|---|
| | V. rupestris | V. vinifera |
| Control | 0.06 | 0.06 |
| 0.3 | 120.9 | 2.02 |
| 0.4 | 236.6 | 3.01 |
| 0.6 | 88.67 | 19.17 |
| 0.8 | 275.91 | 32.04 |
| 1 | 298.13 | 79.51 |
| 1.5 | 106.64 | 121.396 |
| 2 | 292.88 | 92.58 |
| 3 | 344.45 | 98.76 |
| 4 | 116.76 | 171.39 |

TABLE IV

| AlCl$_3$ concentration in % | AMOUNT OF RESVERATROL EXPRESSED IN µg/g OF FRESH EXTRACT OF: | |
|---|---|---|
| | V. rupestris | V. vinifera |
| Control | 0.06 | 0.06 |
| 0.3 | 0.1 | 0.1 |
| 0.4 | 426.63 | 97.67 |
| 0.6 | 37.93 | 47.03 |
| 0.8 | 35.51 | 88.25 |
| 1 | 133.22 | 62.4 |
| 1.5 | 251.1 | 149.14 |
| 2 | | 150.33 |
| 3 | | 184.02 |
| 4 | 199.21 | 174.25 |

TABLE V

| AlCl$_3$ concentration in % | AMOUNT OF RESVERATROL EXPRESSED IN µg/g OF FRESH EXTRACT OF: | |
|---|---|---|
| | V. rupestris | V. vinifera |
| Control | 0.06 | 0.06 |
| 0.6 | 208.11 | 0.10 |
| 0.8 | 547.43 | 188.78 |
| 1 | 138.15 | 47.60 |
| 1.5 | | 188.61 |
| 2 | 41.02 | |
| 3 | 383.00 | |

EXAMPLE 2

Three examples of compositions based on aluminium chloride (in a solid or liquid form), which can be used in the context of the invention, are found below:

Composition n° 1
For 1 kg of powder:

| | |
|---|---|
| AlCl$_3$.6H$_2$O | 0.800 |
| Kaolin | 0.200 |

Composition n° 2
For 1 kg of solution:

| | |
|---|---|
| AlCl$_3$.6H$_2$O | 0.400 |
| Brown algae extract (alga cream) | 0.250 |
| Water | 0.350 |

Composition n° 3
For 1 litre of solution:

| | |
|---|---|
| AlCl$_3$.6H$_2$O | 0.400 |
| Mineral oil | 0.200 |
| Kidan ® (iprodione) Rhône Poulenc | 0.200 |
| Water | 0.200 |

What is claimed is:

1. A method of eliciting resveratrol synthesis in a vine or edible product thereof by applying to said vine an effective amount of aluminum chloride.

2. The method of claim 1, wherein said aluminium chloride is applied via a foliar route.

3. The method of claim 1, wherein said aluminium chloride is applied by injection into a trunk.

4. The method of claim 1, wherein said effective amount of aluminium chloride is between 0.1 kg and 100 kg per hectare of cultivated soil and per treatment.

5. The method of claim 1, wherein said aluminium chloride is hexahydrated.

6. The method of claim 1, additionally comprising preparing a composition containing an effective amount of aluminium chloride incorporated with a carrier or vehicle which is acceptable in agriculture.

7. The method of claim 6, wherein said composition is presented in a solid form or a liquid form.

8. The method of claim 7, wherein said solid form is selected from the group consisting of a powder and granules.

9. The method of claim 7, wherein said liquid form is an aqueous solution.

10. The method of claim 6, wherein said composition also contains at least one additional substance selected from the group consisting of fungicides, insecticides, herbicides, growth hormones, deficiency correcting elements, algae and extracts of algae.

11. The method of claim 6 wherein said composition presented in the form of a solid and contains from 0.2 to 55% by weight of aluminium chloride.

12. A method of eliciting resveratrol synthesis in a plant or edible product thereof comprising preparing a composition in a solid form selected from the group consisting of a powder and granules, said composition containing an effective amount of aluminum chloride incorporated with a carrier or vehicle which is acceptable in agriculture, and applying said composition to said plant.

13. A method of eliciting resveratrol synthesis in a plant and edible product thereof comprising preparing a composition in a solid form, said composition containing from 0.2 to 55% by weight of aluminum chloride in a carrier or vehicle which is acceptable in agriculture, and applying said composition to said plant.

* * * * *